United States Patent
Uhrich et al.

(10) Patent No.: US 6,940,596 B2
(45) Date of Patent: *Sep. 6, 2005

(54) REFRACTIVE FOCUSING ELEMENT FOR SPECTROSCOPIC ELLIPSOMETRY

(75) Inventors: Craig Uhrich, Redwood City, CA (US); Jianhui Chen, Fremont, CA (US)

(73) Assignee: Therma-Wave, Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/967,872

(22) Filed: Oct. 18, 2004

(65) Prior Publication Data

US 2005/0046842 A1 Mar. 3, 2005

Related U.S. Application Data

(63) Continuation of application No. 09/848,733, filed on May 3, 2001, now Pat. No. 6,829,049
(60) Provisional application No. 60/204,253, filed on May 15, 2000.

(51) Int. Cl.[7] .................................................. G01J 4/00
(52) U.S. Cl. ..................................................... 356/369
(58) Field of Search .............................. 356/364–369, 356/630, 325, 327, 326; 250/225; 359/784, 785, 796, 797, 656, 661

(56) References Cited

U.S. PATENT DOCUMENTS

| | | | |
|---|---|---|---|
| 3,486,805 A | 12/1969 | Kobayashi | 350/2 |
| 5,121,255 A | 6/1992 | Hayashi | 359/656 |
| 5,608,526 A | 3/1997 | Piwonka-Corle et al. | 356/369 |
| 5,798,876 A | 8/1998 | Nagano | 359/819 |
| 5,877,859 A | 3/1999 | Aspnes et al. | 356/364 |
| 5,917,594 A | 6/1999 | Norton | 356/327 |
| 6,101,035 A | 8/2000 | Maruyama | 359/565 |
| 6,256,097 B1 | 7/2001 | Wagner | 356/369 |
| 6,515,744 B2 | 2/2003 | Wei | 356/369 |
| 6,549,282 B1 | 4/2003 | Johs et al. | 356/369 |
| 6,829,049 B1 * | 12/2004 | Uhrich et al. | 356/369 |

FOREIGN PATENT DOCUMENTS

| | | | |
|---|---|---|---|
| GB | 36 35 637 A1 | 7/1987 | G02B/7/02 |
| WO | WO 99/02970 | 1/1999 | G01N/21/21 |

OTHER PUBLICATIONS

M.E. El–Ghazzawi et al., "Spectroellipsometry characterization of directly bonded silicon–on–insulator structures," Thin Solid Films, vol. 233 (1993), pp. 218–222.

D.E. Aspnes et al., "High Precision Scanning Ellipsometer," Applied Optics, vol. 14, No. 1, Jan. 1975, pp. 220–228.

* cited by examiner

Primary Examiner—Zandra V. Smith
Assistant Examiner—Gordon J. Stock, Jr.
(74) Attorney, Agent, or Firm—Stallman & Pollock LLP

(57) ABSTRACT

A broadband ellipsometer is disclosed with an all-refractive optical system for focusing a probe beam on a sample. The ellipsometer includes a broadband light source emitting wavelengths in the UV and visible regions of the spectrum. The change in polarization state of the light reflected from the sample is arranged to evaluate characteristics of a sample. The probe beam is focused onto the sample using a composite lens system formed from materials transmissive in the UV and visible wavelengths and arranged to minimize chromatic aberrations. The spot size on the sample can be less than 3 mm and the aberration is such that the focal shift over the range of wavelengths is less than five percent of the mean focal length of the system.

26 Claims, 2 Drawing Sheets

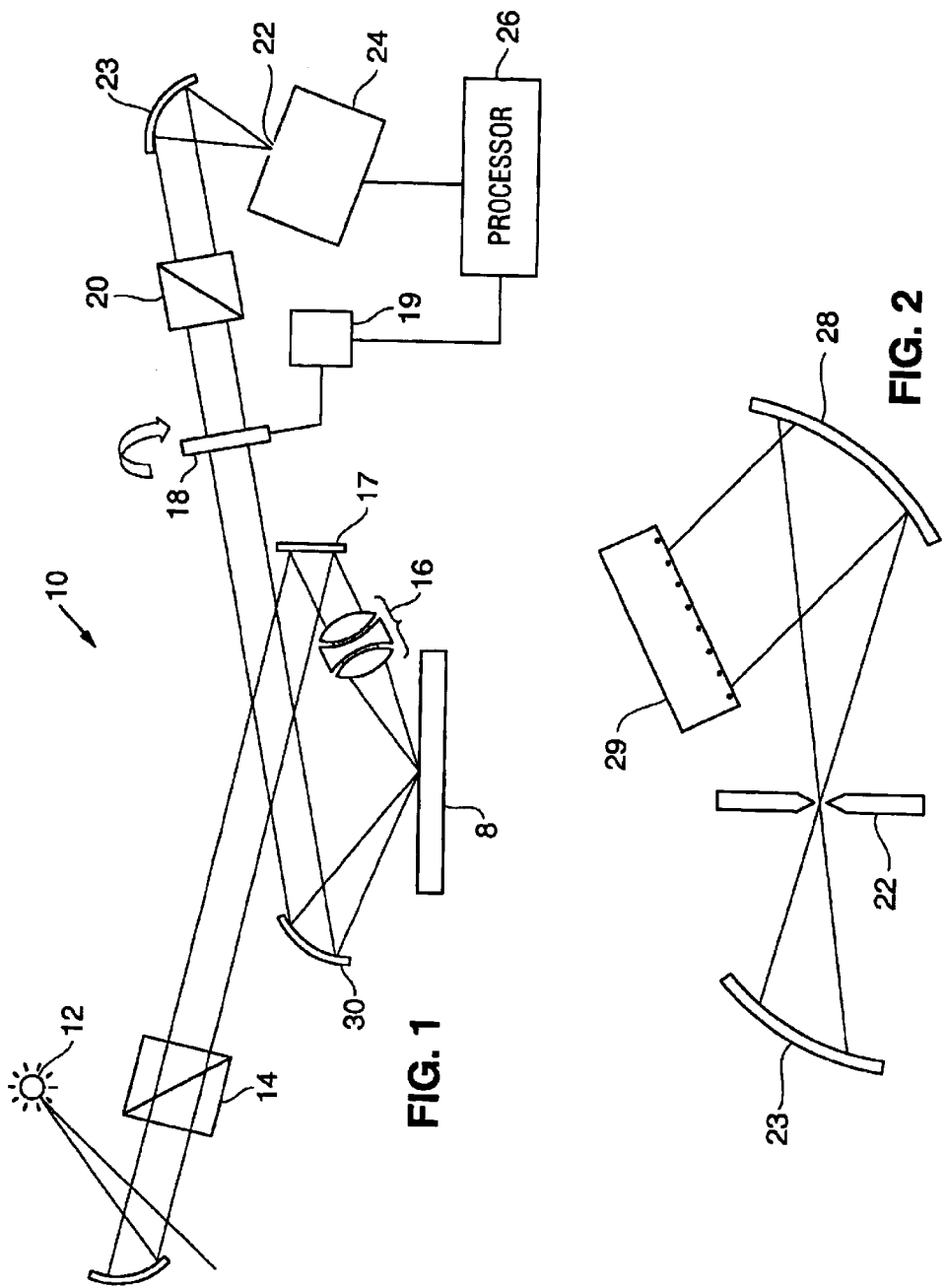

US 6,940,596 B2

REFRACTIVE FOCUSING ELEMENT FOR SPECTROSCOPIC ELLIPSOMETRY

CLAIM OF PRIORITY

This application is a continuation of U.S. patent application Ser. No. 09/848,733, filed May 3, 2001, entitled "SMALL SPOT SPECTROSCOPIC ELLIPSOMETER WITH REFRACTIVE FOCUSING," now U.S. Pat. No. 6,829,049 which claims priority from prior provisional application Ser. No. 60/204,253 filed May 15, 2000, each of which is hereby incorporated herein by reference.

TECHNICAL FIELD OF THE INVENTION

The subject invention relates to spectroscopy ellipsometry. More specifically, the subject invention relates to an ellipsometer which utilizes an all-refractive optics system for focusing a broadband probe beam onto a sample.

BACKGROUND

Ellipsometry is a powerful technique for evaluating thin films on semiconductors. In any ellipsometer, a probe beam having a known polarization state is directed to interact with a sample. Changes in the polarization state induced by the interaction of the probe beam with the sample are then monitored. This information, in the form of Ψ and Δ measurements, is used to analyze characteristics of the sample.

It is well known that in order to improve an ellipsometric analysis, some form of multiple measurements is desirable. This can include taking measurements at multiple angles of incidence or at multiple wavelengths. Spectroscopic ellipsometers using monochrometers to scan the wavelength have been known for many years. For example, see "High Precision Scanning Ellipsometer," by Aspnes and Studna, *Applied Optics*, Vol. 14, No. 1, January 1975.

More recently, efforts have been made to expand the desired wavelength range of spectroscopic ellipsometers into the UV and to obtain measurement data at multiple wavelengths simultaneously. When used in the semiconductor field, broadband probe beams must be focused to a relatively small spot size on the sample surface. Attempts to use lenses (refractive optics) to focus broadband probe beams, and particularly those including UV wavelengths, have run into problems. First, lenses typically have chromatic aberrations. Such aberrations cause the focused distance to be different for different wavelengths. Another problem with lenses is that it was often difficult to find lens materials with good transmission characteristics across a broad wavelength range.

Due to these difficulties, researchers in the prior art began using curved mirrors to focus the broadband probe beam onto the sample surface. Mirrors are advantageous since they can be highly reflective across a broad range of wavelengths. In addition, mirrors exhibit little or no chromatic aberrations. The use of focusing mirrors for a broadband ellipsometer are described in U.S. Pat. No. 4,790,659, issued December 1988, to Erhman, and U.S. Pat. No. 5,608,526, issued Mar. 4, 1997, to Piwonka-Corle.

Unfortunately, while providing a solution for chromatic aberration, mirrors are relatively difficult to align. More specifically, since mirrors must be focused off-axis, any angular error in alignment creates twice that error in beam position. Further, if the mirror is removed from the optics path, a light beam cannot be used to align the rest of the optics path since the mirror is needed to turn the beam. In contrast, the elements of an optics system can be aligned when a focusing lens is removed from the beam path. Another problem with mirrors is that when the probe beam reflects off the mirror, the polarization state of the beam is changed. Such changes must be very accurately and precisely characterized, otherwise they will cause errors in the analysis of the sample.

Accordingly, it would be desirable to have an all-refractive (lens-based) system for focusing a broadband probe beam to a small spot onto a sample surface. Such a system would be easier to align. In addition, any polarization changes in the probe beam induced by the lens system can be more accurately controlled.

BRIEF SUMMARY

In accordance with these objects, the subject invention provides for a spectroscopic ellipsometer which can obtain a small focused beam spot on a sample using all-refractive optics. The spectroscopic ellipsometer is of the type which has at least one broadband light source emitting both UV and visible wavelengths. The source typically has a range of at least 500 nm and preferably covers a wavelength range of about 200 nm to 800 nm.

Light from the broadband source is polarized and then focused onto the sample with an all-refractive optical system. The optical system includes at least two lenses which are transmissive in the UV and visible wavelengths. The curvatures of the lenses are selected to minimize chromatic and spherical aberrations. With respect to the chromatic aberration compensation, the variation in the focal point over the wavelength range (focal shift) should be no more than five percent and preferably less than 2.5 percent of the mean focal length of the optical system. The optical system is intended to focus the beam on the sample to a small spot, on the order of 3 mm or less.

An analyzer system is provided for monitoring the change in polarization state of the reflected beam induced by interaction with the sample. Any conventional analyzer can be used, including rotating analyzer or rotating compensator (waveplate) configurations. In the preferred embodiment, an aperture or spatial filter is provided in the path of the reflected beam to limit the area of the sample investigated. In the preferred embodiment, the spatial filter includes a focusing optical element and an aperture configured to limit the measured region to a spot size of 100 microns or less.

By using an all-refractive optical system for focusing the beam on the sample, problems associated with the alignment of mirrors are eliminated. In addition, the problems associated with changes in the polarization state of the beam induced by the mirrors are also eliminated.

Further objects and advantages will be apparent from the following detailed description taken in conjunction with the drawings in which:

BRIEF DESCRIPTION OF THE DRAWINGS

FIG. 1 is a schematic illustration of a basic layout of the optical elements of a broadband ellipsometer of the subject invention.

FIG. 2 is a schematic illustration of a spectrometer configuration for obtaining simultaneous measurements at a plurality of wavelengths.

DETAILED DESCRIPTION

Figure 3:
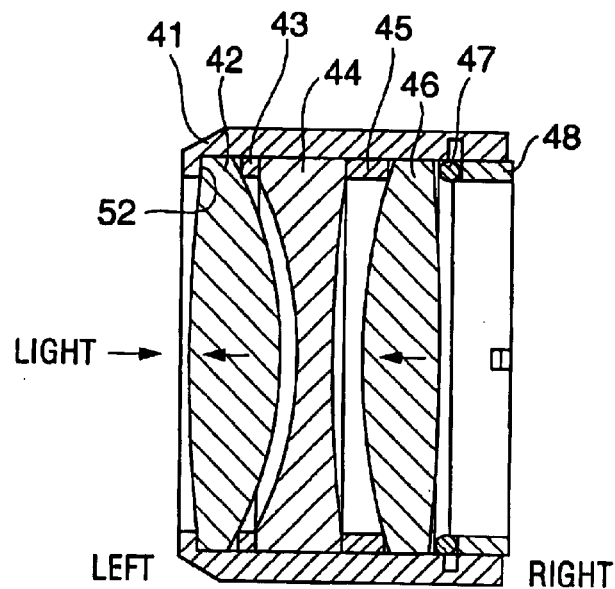
FIG. 3 is a cross-sectional view of an all-refractive optical system for focusing a broadband probe beam on a sample.

Referring to FIG. 1, a broadband ellipsometer 10 formed in accordance with the subject invention is illustrated. The ellipsometer includes a light source 12 for generating a polychromatic beam having both UV and visible wavelengths. This light source can be defined by a single lamp, or by two lamps such as a tungsten halogen for the visible range and a deuterium lamp for the UV wavelengths. The source would typically have a range of at least 500 nm and preferably covers a range from about 200 nm to 800 nm.

In the preferred embodiment, the light is directed through a polarizer 14 for establishing a fixed, known polarization of the light. The light is then directed into the all-refractive lens system 16 of the subject invention, either directly or via one or more turning mirrors 17. These turning mirrors would be essentially planar (flat), rather than curved. The lens system 16 focuses the light on the sample 8.

The light reflected from the sample is collimated by collimator 30. It is passed to an analyzer system for determining the change in polarization state of the beam. In the illustrated embodiment, the analyzer system includes a rotating waveplate (compensator) 18, a stationary analyzer (polarizer) 20 and a detector 24. The waveplate is driven by motor 19. As seen in FIG. 2, the detector is a spectrometer which includes an optical element 28 for dispersing the light (i.e. a grating) and a diode array 29 to measure the different wavelengths simultaneously. As discussed further below, imaging optics, including a focusing element 23 and an aperture 22 can be provided as an input to the detector for controlling the size of the spot on the sample surface which is actually measured. A processor 26 receives the output signals from the detector.

The basic operation of the subject ellipsometer is similar to other broadband ellipsometers and need not be discussed herein. Further information can be obtained from prior patents and applications: U.S. Pat. No. 5,877,859 to Aspnes, et al.; U.S. Pat. No. 5,608,526 to Piwonka-Corle, et al.; and PCT Patent Application No. WO99/02970 to Rosencwaig, et al., all incorporated herein by reference. As can be seen, there are a number of variations in light sources and beam detection (spectrometer) systems. In addition, there are a number of approaches possible for extracting ellipsometric information including rotating polarizers, analyzers and compensators. These elements can be continuously rotated or indexed. In addition, the ellipsometer can be operated as a nulling ellipsometer. The subject invention is intended to be applied to any of these embodiments all of which are well known and understood by those skilled in the art.

Figure 4:
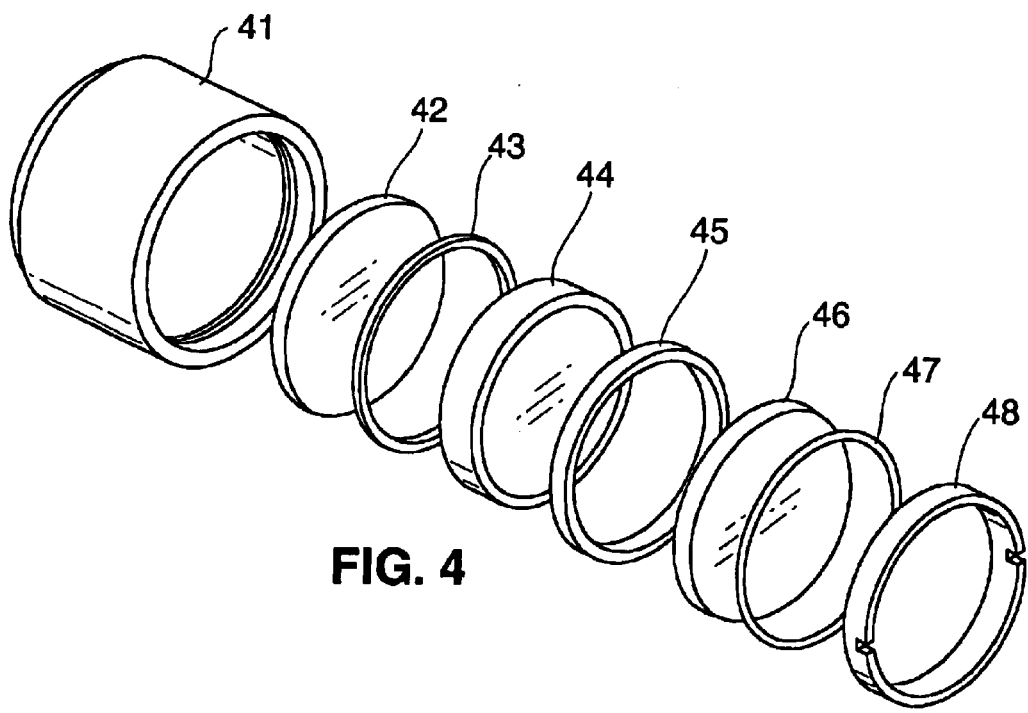
FIG. 4 is an exploded perspective view of the optical elements of FIG. 3.

These various types of ellipsometers can be modified in accordance with the subject invention to include an all-refractive focusing system. A preferred version of such a focusing system is illustrated in FIGS. 3 and 4. This embodiment is defined by a three lens triplet consisting of a pair of calcium fluoride lenses 42, 46 and one fused silica lens 44. These lens materials are substantially transparent in the wavelength region of interest. In the preferred embodiment, the materials are at least 97% transmissive from 190 nm to 900 nm.

At least two lenses of different materials are necessary in order to reduce the chromatic aberration of the system. Chromatic aberration is observed when the focal point for one wavelength is different from the focal point for another wavelength. In a broadband focused system, chromatic aberration has the effect of smearing out the spot on the sample and reducing the amount of light which can be detected and analyzed. The amount of variation in the focal point with respect to the wavelength should be less than five percent of the mean focal length over the range of wavelengths and preferably is less than 2.5 percent.

Chromatic aberration can be reduced by increasing the number of lenses. However, adding lenses can give rise to other problems. Obviously, as more lenses are used, the cost of the optical system will increase. In addition, since each lens can cause polarization changes if not carefully mounted, the complexity of the assembly procedure increases. It is believed that a three lens system strikes a good balance between these countervailing issues. It should be understood that the scope of the subject invention is intended to cover a two lens system as well as systems with four or more lenses.

In the preferred embodiment, lens 42 is positioned on the upstream side of the system and first receives the probe light beam. Lens 42 is a calcium fluoride convex lens. Lens 44 is a fused silica concave lens while lens 46 is a calcium fluoride convex lens. The respective radii of curvature of these lenses and their focal lengths (at 300 nm) are set forth in the table below where the front surface is the face which first receives the probe beam radiation and rear surface is the face where the probe beam emerges.

TABLE 1

| | Radius of Curvature (mm) | | | | Focal |
|---|---|---|---|---|---|
| | Front Surface | Rear Surface | Center Thickness | Material | Length @ 300 nm [mm] |
| Lens 42 | 62.7 | 20.1 | 5 mm | $CaF_2$ | 34.2 |
| Lens 44 | 18.7 | 70.1 | 1.5 mm | Fused Silica | −25.2 |
| Lens 46 | 33.3 | 105.4 | 4 mm | $CaF_2$ | 56.2 |

The spacing between lens 42 and 44 is 1.04 mm. The spacing between lens 44 and 46 is 1.49 mm.

The lenses are mounted in a fixture which stabilizes the lenses and minimizes the stress on the lenses. The optical assembly includes a stainless steel housing 41 with a radial lip 52 on the front end thereof to hold lens 42 in place. Precision metal spacers 43 and 45, formed from an aluminum alloy, separate lenses 42 and 44 and 44 and 46 respectively. A Viton O-ring 47 is sandwiched between the rear surface of lens 46 and retainer ring 48. Retainer ring is threadably engaged with the housing 41.

Proper mounting is important for minimizing stress in the lenses. These stresses induce birefringence which can change the polarization state of the probe beam. These stresses can be minimized if the lens mount does not vary significantly in shape or size due to temperature variations. Stress can also be minimized by using soft materials which contact the lens or by selecting materials and dimensions so that the expansion of the mounts matches the expansion of the lens. In the preferred embodiment, the shape of the spacers is matched to the shape of the lenses so there are no sharp corners hitting the lenses. In addition, the flexible O-ring 47 prevents the lenses from shifting, but provides relief for thermal expansion.

In practice, it has been observed that any stresses that arise in the lenses tend to run generally transversely across the lens. Accordingly, applicant has found that the effect of any residual stress in the lens can be minimized if the axis of the transverse stress is aligned with the axis of the polarizer and/or analyzer of the ellipsometer. An empirical measurement of the lens is made, for example, by using the lens as a sample in a transmissive ellipsometer. The axis of the stress is then noted on the lens and referred to during assembly procedures.

The optical system 16 is intended to create a relatively small spot on the sample surface. For semiconductor applications, the spot size can be less than 5 mm in diameter, should be less than 3 mm in diameter, and preferably is about 1.5 mm in diameter. In the illustrated embodiment, the system will actually create two spatially separate spots of different polarization states. This is because the polarizer 14 is a Rochon prism which causes one polarization to be angularly deviated with respect to the other polarization such that two separate beams are created. Each beam is focused at a spatially separate spot on the sample.

The imaging optics are arranged to collect light from only one of the two spots. The imaging optics includes the collimator 30, focusing mirror 23 and the aperture 22. Focusing mirror 23 relays an image of the sample into the plane of the aperture 22. The aperture 22 is sized to transmit only a small portion of the illuminated area. In the preferred embodiment, the area imaged should be less than 100 microns and preferably on the order of 60 microns.

Analysis of the data can be performed using conventional modeling approaches. For example, a theoretical model is set up which corresponds to the actual sample, including a substrate and one or more thin film layers. This model is then used in conjunction with the Fresnel equations to calculate expected measurement data. This theoretical calculated data is then compared to the actual measured data. Differences between the calculated data and the actual measured data are then used to vary the expected characteristics of the sample in an iterative process for determining the actual composition of the sample.

While the subject invention has been described with reference to a preferred embodiment, various changes and modifications could be made therein, by one skilled in the art, without varying from the scope and spirit of the subject invention as defined by the appended claims.

What is claimed is:

1. A broadband ellipsometer for evaluating the characteristics of a sample, comprising:
   a broadband light source for generating a polychromatic probe beam;
   an all-refractive focusing optical system for focusing the probe beam, said all-refractive focusing optical system having at least three lenses including two convex calcium fluoride lenses disposed on opposing sides of a concave fused silica lens; and
   an analyzer system for monitoring a portion of the probe beam light reflected from the sample.

2. An ellipsometer according to claim 1, wherein:
   the probe beam contains UV and visible wavelengths, and the lenses are transparent to both UV and visible wavelengths.

3. An ellipsometer according to claim 1, wherein:
   the lenses have refractive powers selected to reduce chromatic aberration of the optical system such that the focal shift over the range of wavelengths is less than five percent of the mean focal length of the optical system.

4. An ellipsometer according to claim 1, further comprising:
   a processor for evaluating characteristics of the sample based on output signals generated by the analyzer system.

5. An ellipsometer according to claim 4, wherein:
   the processor operates to determine a change in polarization state of the polychromatic probe beam at a plurality of wavelengths to derive ellipsometric information.

6. An ellipsometer according to claim 1, wherein:
   the optical system further includes a lens mounting fixture for minimizing stress on the lenses in order to minimize induced birefringence.

7. An ellipsometer according to claim 1, wherein:
   the probe beam is focused to a spot on the surface of the sample having a diameter that is less than 5 mm in diameter.

8. An ellipsometer according to claim 1, wherein:
   the probe beam is focused to a spot on the surface of the sample having a diameter that is less than 3 mm in diameter.

9. An ellipsometer according to claim 1, further comprising:
   an imaging system for transmitting a portion of the probe beam light reflected from the sample to a detector of the analyzer system.

10. An ellipsometer according to claim 9, wherein:
    the portion of the probe beam transmitted by the imaging system corresponds to area on the sample less than 100 microns in diameter.

11. An ellipsometer according to claim 9, wherein:
    the portion of the probe beam transmitted by the imaging system corresponds to area on the sample less than 60 microns in diameter.

12. An ellipsometer according to claim 9, wherein:
    the imaging system further includes an aperture between the sample and the detector.

13. An ellipsometer according to claim 1, wherein:
    the probe beam has wavelength components spanning at least 500 nanometers.

14. An ellipsometer according to claim 1, wherein:
    the probe beam has wavelength components spanning 200 nm to 800 nm.

15. An ellipsometer according to claim 1, further comprising:
    a polarizer, wherein the lenses are aligned such that the transverse stresses in the lenses are aligned with an optical axis of the polarizer.

16. An ellipsometer according to claim 1, wherein:
    the analyzer system generates output signals corresponding to a plurality of wavelengths.

17. A broadband ellipsometer for evaluating the characteristics of a sample, comprising:
    a broadband light source for generating a polychromatic probe beam, said probe beam having UV and visible wavelengths having a wavelength range of at least 500 nm;
    an all-refractive focusing optical system for focusing the probe beam to a spot on the surface of the sample having a diameter less than 5 mm, said all-refractive focusing optical system including at least three lenses that are transparent to both UV and visible wavelengths, the lenses including two convex calcium fluoride lenses disposed on opposing sides of a concave fused silica lens; and
    an analyzer system for monitoring a portion of the probe beam light reflected from the sample.

18. An ellipsometer according to claim 17, wherein:
    the lenses are transparent to both UV and visible wavelengths.

19. An ellipsometer according to claim 17, wherein:

the lenses have refractive powers selected to reduce chromatic aberration of the optical system such that the focal shift over the range of wavelengths is less than five percent of the mean focal length of the optical system.

20. An ellipsometer according to claim 17, further comprising:

a processor for evaluating characteristics of the sample based on output signals generated by the analyzer system.

21. An ellipsometer according to claim 20, wherein:

the processor operates to determine a change in polarization state of the polychromatic probe beam at a plurality of wavelengths to derive ellipsometric information.

22. An ellipsometer according to claim 17, wherein:

the optical system further includes a lens mounting fixture for minimizing stress on the lenses in order to minimize induced birefringence.

23. An ellipsometer according to claim 1, further comprising:

an imaging system for transmitting a portion of the probe beam light reflected from the sample to a detector of the analyzer system.

24. An ellipsometer according to claim 23, wherein:

the portion of the probe beam transmitted by the imaging system corresponds to area on the sample less than 100 microns in diameter.

25. An ellipsometer according to claim 23, wherein:

the portion of the probe beam transmitted by the imaging system corresponds to area on the sample less than 60 microns in diameter.

26. An ellipsometer according to claim 23, wherein:

the imaging system further includes an aperture between the sample and the detector.

* * * * *